US009582988B2

(12) United States Patent
Gross

(10) Patent No.: US 9,582,988 B2
(45) Date of Patent: Feb. 28, 2017

(54) METHOD AND SYSTEM TO REDUCE THE NUISANCE ALARM LOAD IN THE CLINICAL SETTING

(71) Applicant: KONINKLIJKE PHILIPS N.V., Eindhoven (NL)

(72) Inventor: Brian David Gross, North Andover, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/647,211

(22) PCT Filed: Nov. 20, 2013

(86) PCT No.: PCT/IB2013/060260
§ 371 (c)(1),
(2) Date: May 26, 2015

(87) PCT Pub. No.: WO2014/087288
PCT Pub. Date: Jun. 12, 2014

(65) Prior Publication Data
US 2015/0310733 A1    Oct. 29, 2015

Related U.S. Application Data

(60) Provisional application No. 61/733,131, filed on Dec. 4, 2012.

(51) Int. Cl.
G08B 29/00 (2006.01)
G08B 29/18 (2006.01)
(Continued)

(52) U.S. Cl.
CPC ......... *G08B 29/185* (2013.01); *A61B 5/02455* (2013.01); *A61B 5/746* (2013.01);
(Continued)

(58) Field of Classification Search
CPC . A61B 5/746; A61B 5/02455; G06F 19/3406; G06F 19/327; G06F 19/322
(Continued)

(56) References Cited

U.S. PATENT DOCUMENTS 5,438,983 A * 8/1995 Falcone ............... A61B 5/746
340/573.1
7,301,451 B2  11/2007 Hastings
(Continued)

OTHER PUBLICATIONS

Curtis, D. W., et al.; SMART—An Integrated Wireless System for Monitoring Unattended Patients; 2008; J. Am. Med. Inform. Assoc.; 15(1)44-53.
(Continued)

*Primary Examiner* — John A Tweel, Jr.

(57) ABSTRACT

A medical method and corresponding system for determining outlying patients in a data set of patient physiological alarms. Physiological alarms for patients are received and/or generated. An alarm rate limit for the patients, and/or alarm response limits for clinician response times, are determined based on a clinical alarm management policy. The received and/or generated physiological alarms are analyzed to determine at least one of: 1) patients exceeding the alarm rate limit; and 2) clinicians exceeding the alarm response limits.

20 Claims, 2 Drawing Sheets

(51) Int. Cl.
- *A61B 5/0245* (2006.01)
- *A61B 5/00* (2006.01)
- *G06F 19/00* (2011.01)
- *G08B 29/02* (2006.01)

(52) U.S. Cl.
CPC .......... *G06F 19/322* (2013.01); *G06F 19/327* (2013.01); *G06F 19/3406* (2013.01); *G08B 29/02* (2013.01)

(58) Field of Classification Search
USPC .................. 340/506, 573.1; 600/300, 301
See application file for complete search history.

(56) References Cited

U.S. PATENT DOCUMENTS

| | | | | |
|---|---|---|---|---|
| 8,400,290 | B2 * | 3/2013 | Baker, Jr. .......... | A61M 16/0051 600/300 |
| 8,648,707 | B2 * | 2/2014 | Franz ................. | G06F 19/3406 340/573.1 |
| 9,095,316 | B2 * | 8/2015 | Welch ................... | A61B 5/746 |
| 9,098,604 | B2 * | 8/2015 | Treacy ................. | G06F 19/327 |
| 2004/0236187 | A1 * | 11/2004 | Bock ................. | A61B 5/02455 600/300 |
| 2005/0151640 | A1 | 7/2005 | Hastings | |
| 2009/0275807 | A1 * | 11/2009 | Sitzman ................ | A61B 5/746 600/301 |

OTHER PUBLICATIONS

Cvach, M.; Monitor Alarm Fatigue: An Integrative Review; Jul./Aug. 2012; Biomedical Instrumentation & Technology; pp. 268-277.

* cited by examiner

METHOD AND SYSTEM TO REDUCE THE NUISANCE ALARM LOAD IN THE CLINICAL SETTING

CROSS REFERENCE TO RELATED APPLICATIONS

This application is a national filing of PCT application Serial No. PCT/IB2013/060260, filed Nov. 20, 2013, published as WO 2014/087288 A1 on Jun. 12, 2014, which claims the benefit of U.S. provisional application Ser. No. 61/733,131 filed Dec. 4, 2012, which is incorporated herein by reference.

The present application relates generally to patient monitoring. It finds particular application in conjunction with reducing alarm fatigue and will be described with particular reference thereto. However, it is to be understood that it also finds application in other usage scenarios and is not necessarily limited to the aforementioned application.

Alarm fatigue is the condition in which clinicians at medical institutions become desensitized to clinical alarms because of the high probability that the alarms are not of actual clinical significance. Alarm fatigue impedes patient care and in some cases becomes a hazard. Alarm fatigue typically results from inappropriate alarm settings for a given patient, noisy sensor signals, or alarm algorithm deficiencies. Most solutions to mitigating alarm fatigue are based on reducing the sensitivity of alarms for every patient. For example, alarm limits can be widened or the number of physiological parameters that generate alarms can be reduced. However, not every patient will benefit from this approach to reducing alarm fatigue. Reducing the sensitivity of alarms increases the likelihood that clinically significant alarms will not be generated.

The present application provides new and improved methods and systems which overcome the above-referenced problems and others.

In accordance with one aspect, a medical system is provided. The medical system includes at least one processor programmed to receive and/or generate physiological alarms for patients. The processor is further programmed to establish an alarm rate limit for the patients, and/or alarm response limits for clinician response times, based on a clinical alarm management policy. Even more, the processor is programmed to analyze the received and/or generated physiological alarms to determine at least one of: patients exceeding the alarm rate limit; and clinicians exceeding the alarm response limits.

In accordance with another aspect, a medical method is provided. Physiological alarms for patients are received and/or generated. An alarm rate limit for the patients, and/or alarm response limits for clinician response times, are established based on a clinical alarm management policy. The received and/or generated physiological alarms are analyzed to determine at least one of: patients exceeding the alarm rate limit; and clinicians exceeding the alarm response limits.

In accordance with another aspect, a medical system is provided. The medical system includes a plurality of patient monitors each associated with a patient and each including one or more sensors to collect physiological data of the patient. The plurality of patient monitors are configured to one or more of: 1) transmit physiological alarms based on the physiological data to a central station; and 2) transmit the physiological data to the central station. The medical system further includes the central station, which includes at least one processor. The processor is programmed to one or more of: 1) receive the physiological alarms from the plurality of patient monitors; and 2) receive the physiological data from the plurality of patient monitors and generate physiological alarms based on the received physiological data. The processor is further programmed to establish an alarm rate limit for the patients, and/or alarm response limits for clinician response times, based on a clinical alarm management policy. Further, the processor is programmed to analyze the received and/or generated physiological alarms to determine at least one of: patients exceeding the alarm rate limit; and clinicians exceeding the alarm response limits.

One advantage resides in reduced alarm fatigue.

Another advantage resides in improved patient care.

Another advantage resides in improved quality assurance reporting.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Research has indicated that there are a small number of patients who are responsible for most of the alarm load on a given day. The present invention builds on this to provide a new approach for mitigating alarm fatigue that does not require reducing the sensitivity for all patients. According to the approach, those patients which need attention are identified. A need for attention can be based on a lack of responsiveness to alarms by clinicians or the frequency and duration of alarms. Once the patients needing attention are identified, clinicians can focus on them to reduce alarm load.

Figure 1:
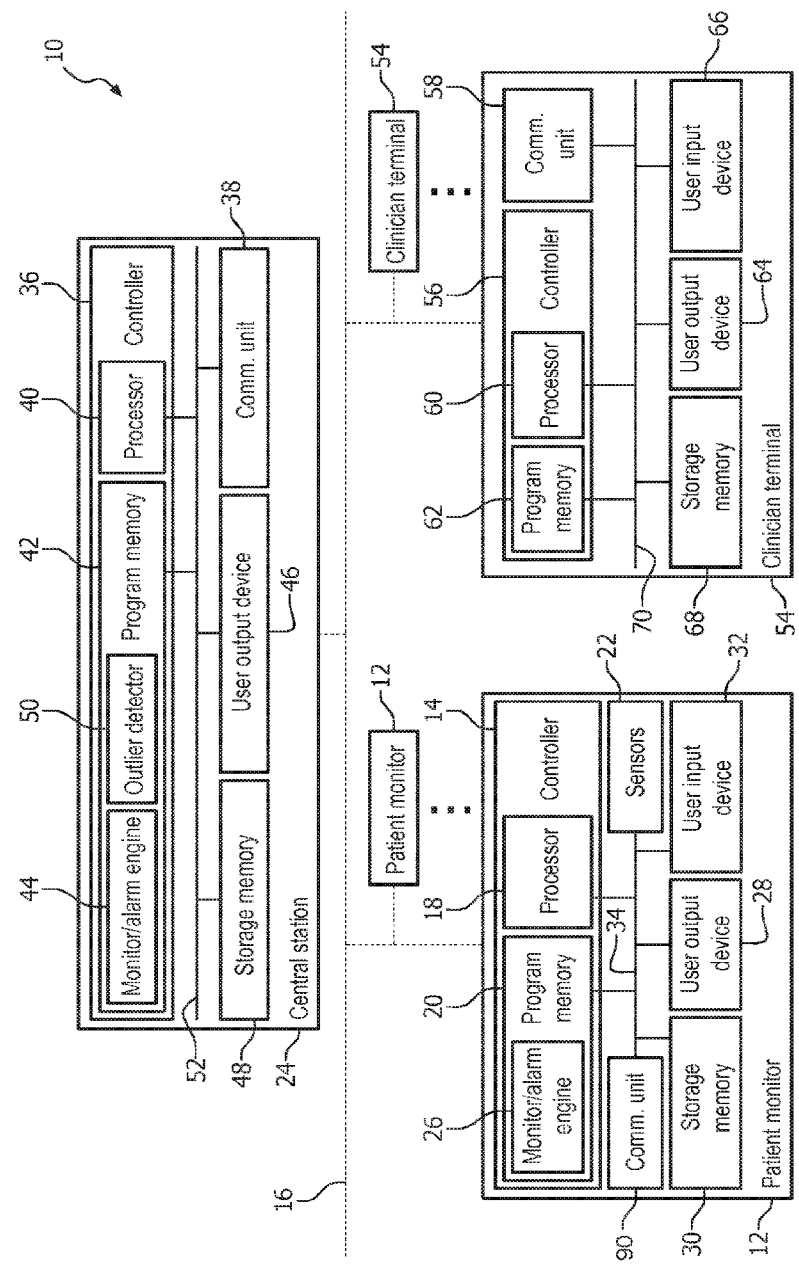
FIG. 1 illustrates a medical system for patient monitoring.

With reference to FIG. 1, a medical system 10 is provided. The medical system 10 includes one or more patient monitors 12. The patient monitors 12 are configured to monitor and/or facilitate monitoring of patients for physiological conditions requiring clinician intervention, such as cardiac dysrhythmia. The patient monitors 12 are each associated with a patient and positioned on, within or proximate to the patient. For example, at least one of the patient monitors 12 could be a bedside monitor.

Each of the patient monitors 12 includes a controller 14 and a communication unit 90. The communication unit 90 allows the controller 14 to communicate with external devices and/or systems, for example, over a communication network 16, such as a the Internet or a local area network. The controller 14 includes at least one processor 18 and at least one program memory 20. The program memory 20 includes processor executable instructions executed by the processor 18 to perform the below described functions of the controller 14.

The controller 14 collects physiological data for one or more physiological parameters of the patient, typically from one or more sensors 22 of the patient monitor 12 and/or external devices and/or systems. Physiological parameters include, for example, heart rate, respiration rate, blood pressure, electrocardiography (ECG) signals, and so forth. The sensors 22 typically includes sensors disposed on the exterior of the patient, such as on-body and/or wearable sensors. However, the sensors 22 can additionally or alternatively include sensors disposed within the patient and/or proximate to the patient. The physiological data is typically collected continuously in real-time, but it can also be collected periodically.

The controller 14 further performs at least one of: 1) locally monitoring the collected physiological data and generating alarms based thereon; and 2) transmitting the collected physiological data to a central station 24 of the medical system 10 over the communication network 16. As to locally monitoring the collected physiological data, the controller 14 includes a monitor and/or alarm engine 26. The monitor and/or alarm engine 26 is a software module of processor executable instructions stored on the program memory 20 and executed by the processor 18.

The monitor and/or alarm engine 26 monitors the collected physiological data and generates alarms based thereon. The monitor and/or alarm engine 26 can generate alarms by matching alarm criteria to the collected physiological data and generating an alarm if a match is found. For example, an alarm can be issued if a physiological parameter exceeds a parameter-specific threshold. The alarm criteria can take in to account present values of physiological parameters, as well as trends of physiological parameters. The monitor and/or alarm engine 26 can also generate alarms based on long-term patient health condition prediction. After generating an alarm, the alarm can be presented to a clinician on a user output device 28 of the patient monitor 12. For example, the alarm can be displayed to the clinician. The alarm can also be transmitted to the central station 24.

As to transferring the collected physiological data, the controller 14 can immediately transmit the received physiological data to the central station 24 upon receiving it. Alternatively, the controller 14 can buffer or otherwise store the received physiological data in a storage memory 30 of the patient monitor 12 and only transmit the buffered physiological data when the amount exceeds a threshold.

The controller 14 can further present alarms and/or other messages from the central station 24 to clinicians on the user output device 28. Other messages include, for example, identification of patients needing attention. Even more, the controller 14 can present the captured physiological data to clinicians on the user output device 28. For example, the present values of physiological parameters and/or trends for physiological parameters can be displayed. The controller 14 can further allow clinicians to manipulate the presented data, such as the captured physiological data and/or the alarms and/or other messages, using a user input device 32 of the patient monitor 12.

At least one system bus 34 of the patient monitor 12 interconnects the program memory 20, the processor 18 and the communication unit 90. Further, the system bus 34 can be employed to interconnect at least one of the storage memory 30, the user input device 32, the user output device 28, and the sensors 22 with the program memory 20, the processor 18 and the communication unit 90. The remaining components can communicate with the components interconnected by the system bus 34 by way of the communication unit 90. Further, although the components of the patient monitor 12, other than the processor 18 and the program memory 20, are illustrated as external to the controller 14, one or more of these components can be integrated with the controller 14.

The central station 24 is central to the patient monitors 12 and configured to monitor the patients for physiological conditions and/or to identify patients in need of attention. The central station 24 includes a controller 36 and a communication unit 38. The communication unit 38 allows the controller 36 to communicate with external devices and/or systems over the communication network 16. For example, the communication unit 38 allows the controller 36 to communicate with the patient monitors 12 over the communication network 16. The controller 36 includes at least one processor 40 and at least one program memory 42. The program memory 42 includes processor executable instructions executed by the processor 40 to perform the below described functions of the controller 36.

The controller 36 at least one of: 1) receives the alarms generated by the patient monitors 12; and 2) receives the physiological data collected by the patient monitors 12. As to receiving physiological data, the controller 36 locally monitors the received physiological data and generates alarms based thereon using a monitor and/or alarm engine 44. The monitor and/or alarm 44 engine is a software module of processor executable instructions stored on the program memory 42 and executed by the processor 40.

The monitor and/or alarm engine 44 monitors the collected physiological data and generates alarms based thereon. The monitor and/or alarm engine 44 can generate alarms by matching alarm criteria to the collected physiological data and generating an alarm if a match is found. The alarm criteria can take in to account present values of physiological parameters, as well as trends of physiological parameters. The monitor and/or alarm engine 44 can also generate alarms based on long-term patient health condition prediction.

After generating an alarm, the alarm can be presented to a clinician on a user output device 46 of the central station 24 or some other device and/or system of the medical system 10. For example, the alarm can be transmitted to the patient monitor 12 that provided the central station 24 with the physiological data that resulted in the alarm, and the patient monitor 12 can display the alarm to a clinician on the user output device 28 of the patient monitor 12.

The received and/or generated alarms are typically stored in a storage memory 48 of the central station 24. For each alarm stored, one or more of the following are stored: 1) the one or more parameter sources corresponding to the one or more parameter values causing the alarm (e.g., the pulse oximeter at the bedside monitor); 2) the duration of the alarm (e.g., the time between the start of the alarm condition and the end of the alarm condition); 3) the acknowledgment time (e.g., when a clinician acknowledged the alarm); 4) the onset time (e.g., when the alarm is generated); 5) the one or more parameter trends corresponding to the one or more parameters; 6) the clinician assigned to the patient corresponding to the alarm; and 7) inoperative condition history for the one or more parameters.

The controller 36 further detects outlying patients among the stored alarms using an outlier detector 50. The outlier detector 50 is a software module of processor executable instructions stored on the program memory 42 and executed by the processor 40. The outlier detector 50 is configured to identify those patients which need attention and notify clinicians. A need for attention can be based on a lack of responsiveness to alarms by clinicians or the frequency and duration of alarms.

Figure 2:
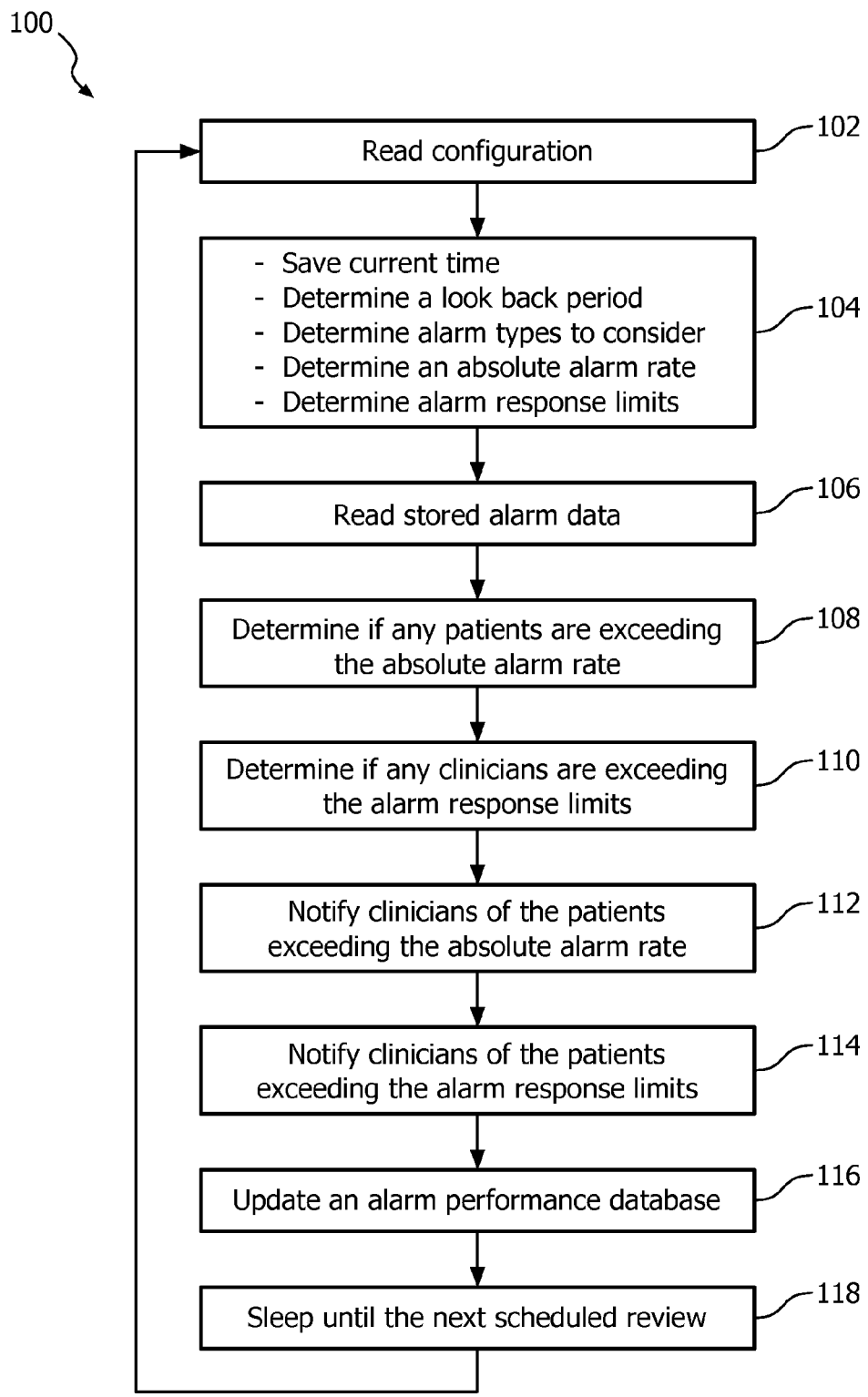
FIG. 2 illustrates a flowchart of a routine for identifying outlying patients to reduce alarm loads.

With reference to FIG. 2, a routine 100 for identifying those patients which need attention is illustrated. The routine 100 is suitably performed iteratively by the outlier detector 50. The number of iterations and the time between iterations is controlled by a schedule for performing the routine defined by an operator of the central station 24. The schedule can be based on, for example, the computing resources of the central station 24 and/or the quantity of received and/or generated alarms.

For each iteration, a configuration is read 102. The configuration identifies the clinical alarm management policy for the medical institution running the routine 100. The clinical alarm management policy defines the policy of the medical institution maintaining the medical system 10 for clinical alarms. The configuration can identify one or more of types of alarms (i.e., alarm conditions) to consider, the acceptable time for a clinician to acknowledge an alarm, the expected time for the event triggering an alarm to correct itself, acceptable limits for the parameters of an alarm, and the target number of alarms during a given period of time.

After reading 102 the configuration, the routine is initialized 104. The current time is saved and the amount time to look back is determined. The amount time to look back is typically the difference between the current time and the saved time of the last iteration. Further, the types of alarms to consider, an absolute alarm rate and alarm response limits for clinicians are determined from the configuration. The absolute alarm rate can, for example, be based on the target number of alarms and the amount of time to look back. The alarm response limits can, for example, be individual to different types of alarms and/or common to the alarms considered.

The stored alarms which fall within the look back period and which fall within the types of alarms to consider are then identified 106 and analyzed 108, 110. In analyzing these alarms, a determination 108 is made as to whether any patients are exceeding the absolute alarm rate. This includes determining the alarm rate for each patient and comparing it to the absolute alarm rate. The alarm rate for a patient can be determined by, for example, counting the alarms corresponding the patient to determine a total number of alarms. The total is then divided by the number of time units of the absolute alarm rate which fall within the look back period. In addition to or as an alternative to the determination 108 regarding alarm rate, a determination 110 is made as to whether any clinicians are exceeding the alarm response limits. For each alarm under consideration, the acknowledge time of the alarm is compared to corresponding alarm response limit.

Based on the analysis 108, 110, notifications are sent 112, 114 to the clinicians. Clinicians with patients in their care that have alarm rates exceeding the absolute alarm rate are notified 112 of these patients. Further, clinicians with patients in their care that have acknowledge times exceeding the alarm response limits are notified 114 of these patients. The notifications can identify data stored with the alarms, such as the time at the patient. Further, the notification to the clinicians can be presented to the clinicians by way of any of the devices and/or systems of the medical system 10, such as the central station 24 and the patient monitors 12. This can include the use of text messages, emails, a marquee and other communication mechanisms.

A performance database of the storage memory 48 is further updated with the results of the analysis. The results can include the number of outlier patients (i.e., the number of patients with excessive alarm rates plus the number of patients with excessive clinician response times). The results can further include the clinicians who have patients with excessive alarm rates and/or the clinicians who have excessive response times. Once the performance database is updated, the outlier detector 50 sleeps until the next scheduled iteration.

The performance database can be employed to assess the quality of care by the clinicians. In that regard, clinicians can undergo targeted education based on their performance. For example, clinicians with excessive response times or excessive alarm rates can be better trained to reduce the alarms. The performance database can further be analyzed by a recommendation generator (a software module of the program memory 42) to generate recommendations for the clinicians. For example, the recommendation generator can recommend reducing the alarm sensitivity for patients identified as having excessive alarm rates.

At least one system bus 52 of the central station 24 interconnects the program memory 42, the processor 40 and the communication unit 38. Further, the system bus 52 can be employed to interconnect at least one of the storage memory 48 and the user output device 46 with the program memory 42, the processor 40 and the communication unit 38. The remaining components can communicate with the components interconnected by the system bus 52 by way of the communication unit 38. Further, although the components of the central station 24, other than the processor 40 and the program memory 42, are illustrated as external to the controller 36, one or more of these components can be integrated with the controller 36.

One or more clinician terminals 54 allow clinicians to interface with other devices and/or systems of the medical system 10 over the communication network 16, such as the central station 24 and/or the patient monitors 12. By interfacing with the other devices and/or systems, clinicians can receive physiological data and/or alarms and/or other messages. Examples of the caregiver terminals include desktop computers, laptops, tablets, smartphones, pagers, and so on.

Each of the clinician terminals 54 includes a controller 56 and a communication unit 58. The communication unit 58 allows the controller 56 to communicate with devices and/or systems over the communication network 16. The controller 56 includes at least one processor 60 and at least one program memory 62. The program memory 62 includes processor executable instructions executed by the processor 60 to perform the following functions of the controller 56.

The controller 56 can present alarms and/or other messages from the central station 24 to clinicians on a user output device 64 of the clinician terminal 54. Other messages include, for example, identification of patients needing attention. Even more, the controller 56 can present the captured physiological data to clinicians on the user output device 64. For example, the present values of physiological parameters and/or trends for physiological parameters can be displayed. The controller 56 can further allow clinicians to manipulate the presented data, such as the captured physiological data and/or the alarms and/or other messages, using a user input device 66 of the clinician terminal 54.

The controller 56 can further store the data received from the communication network, such as alarms and/or other messages, in a storage memory 68 of the clinician terminal 54. A clinician can then recall the stored data for later use without the need for a connection to the communication network 16.

At least one system bus 70 of the clinician terminal 54 interconnects the program memory 62, the processor 60 and the communication unit 58. Further, the system bus 70 can be employed to interconnect at least one of the storage memory 68, the user input device 66 and the user output device 64 with the program memory 62, the processor 60 and the communication unit 58. The remaining components can communicate with the components interconnected by the system bus 70 by way of the communication unit 58.

Further, although the components of the clinician terminal 54, other than the processor 60 and the program memory 62, are illustrated as external to the controller 56, one or more of these components can be integrated with the controller 56.

Notwithstanding that the patient monitors 12, central station 24 and clinician terminals 54 have been described discretely, it is to be appreciated that there can be overlap between these systems and/or devices. For example, one of the patient monitors 12 can also serve as one of the clinician terminals 54 and vice versa. Further, although the outlier detector 50 was described in connection with the central station 24, it also finds application in other systems and/or devices, such as floor surveillance and/or population management systems and/or devices. For example, the outlier detector 50 can be remote from the central station 24 and access the information stored in the storage memory 48 remotely.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a controller includes: 1) at least one memory with processor executable instructions to perform the functionality of the controller; and 2) at least one processor executing the processor executable instructions; a user output device includes a printer, a display device, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A medical system comprising:
at least one processor programmed to:
receive and/or generate physiological alarms for patients;
establish an alarm rate limit for the patients, and alarm response time limits for clinician response times, based on a clinical alarm management policy;
store the received and/or generated alarms for subsequent analysis wherein each stored alarm includes at least a response time and a clinician assigned to a patient corresponding to the alarm;
analyze the stored physiological alarms to determine:
patients exceeding the alarm rate limit; and,
clinicians exceeding the alarm response limits; and
notify clinicians of (i) patients in their care that have alarm rates exceeding the alarm rate limit and (ii) patients in their care that have alarm response times exceeding the alarm response time limits.

2. The medical system according to claim 1, wherein the processor is further programmed to:
notify clinicians exceeding the alarm response limits that they are exceeding the alarm response limits.

3. The medical system according to claim 1, wherein each stored alarm further includes one or more of: one or more parameter sources corresponding to one or more parameters causing the alarm; duration of the alarm; onset time of the alarm; and one or more parameter trends corresponding to the one or more parameters.

4. The medical system according to claim 1, wherein the analysis is iteratively performed for a subset of the stored alarms spanning a look back period.

5. The medical system according to claim 1, wherein the clinical alarm management policy defines the policy of a medical institution maintaining the medical system for clinical alarms.

6. The medical system according to claim 1, wherein the processor is further programmed to:
store at least one of: 1) a listing of patients exceeding the alarm rate limit; and
2) a listing of clinicians exceeding the alarm response limits.

7. The medical system according to claim 1, wherein the alarm rate limit is based on a target number of alarms.

8. The medical system according to claim 1, further including:
one or more patient monitors generating at least one of the physiological alarms for the patients.

9. A medical method, performed by one or more processors, the method comprising:
receiving and/or generating physiological alarms for patients;
establishing an alarm rate limit for the patients, and/or alarm response limits for clinician response times, based on a clinical alarm management policy;
analyzing the received and/or generated physiological alarms to determine at least one of:
patients exceeding the alarm rate limit; and,
clinicians exceeding the alarm response limits; and
storing a listing of clinicians exceeding the alarm response limits.

10. The medical method according to claim 9, further including notifying clinicians with patients exceeding the alarm rate limit of these patients.

11. The medical method according to claim 9, further including:
notifying clinicians exceeding the alarm response limits that they are exceeding the alarm response limits.

12. The medical method according to claim 9, further including:
storing the received and/or generated alarms for subsequent analysis.

13. The medical method according to claim 12, wherein the analysis is iteratively performed for a subset of the stored alarms spanning a look back period.

14. The medical method according to claim 9, wherein the clinical alarm management policy defines the policy of a medical institution maintaining the medical system for clinical alarms.

15. The medical method according to claim 9, further including:
storing a listing of patients exceeding the alarm rate limit.

16. The medical method according to claim 9, wherein the alarm rate limit is based on a target number of alarms.

17. At least one processor configured to perform the method according to claim 9.

18. A medical system comprising:
a plurality of patient monitors each associated with a patient and each including one or more sensors to collect physiological data of the patient, the plurality of patient monitors configured to one or more of: 1) transmit physiological alarms based on the physiological data to a central station; and 2) transmit the physiological data to the central station;

the central station including at least one processor programmed to:

one or more of: 1) receive the physiological alarms from the plurality of patient monitors; and 2) receive the physiological data from the plurality of patient monitors and generate physiological alarms based on the received physiological data;

establish alarm response limits for clinician response times, based on a clinical alarm management policy;

analyze the received and/or generated physiological alarms to determine clinicians exceeding the alarm response limits; and store a listing of clinicians exceeding the alarm response limits.

19. The medical system according to claim 1, further comprising an output device configured to display the notifications to clinicians of (i) patients in their care that have alarm rates exceeding the alarm rate limit and (ii) patients in their care that have alarm response times exceeding the alarm response time limits.

20. The medical method according to claim 12, wherein each stored alarm includes a duration of the alarm and a clinician acknowledgment time of the alarm.

\* \* \* \* \*